United States Patent [19]

Hirschfeld

[11] Patent Number: 4,599,901
[45] Date of Patent: Jul. 15, 1986

[54] PRESSURE-SENSITIVE OPTRODE

[75] Inventor: Tomas B. Hirschfeld, Livermore, Calif.

[73] Assignee: University of California, Berkeley, Calif.

[21] Appl. No.: 675,633

[22] Filed: Nov. 28, 1984

Related U.S. Application Data

[63] Continuation-in-part of Ser. No. 430,578, Sep. 30, 1982, Pat. No. 4,509,370.

[51] Int. Cl.$^4$ .............................................. G01L 7/08
[52] U.S. Cl. ...................................... 73/705; 73/723; 250/227; 250/231 P
[58] Field of Search ................. 73/705, 35, 723, 715, 73/729, 731; 250/231 P, 227

[56] References Cited

U.S. PATENT DOCUMENTS

| | | | |
|---|---|---|---|
| 4,075,493 | 2/1978 | Wickersheim | 250/461 R |
| 4,200,110 | 4/1980 | Peterson et al. | 128/634 |
| 4,215,275 | 7/1980 | Wickersheim | 250/459 |
| 4,245,507 | 1/1981 | Samulski | 73/356 |
| 4,344,438 | 8/1982 | Schultz | 128/634 |
| 4,447,546 | 5/1984 | Hirschfeld | 436/527 |
| 4,492,121 | 1/1985 | Lehto | 73/705 |
| 4,509,370 | 4/1985 | Hirschfeld | 73/705 |

FOREIGN PATENT DOCUMENTS 82303803.9 7/1982 European Pat. Off. .

OTHER PUBLICATIONS

Wickersheim et al, *Industrial Research and Development*, Dec. 1979.

*Primary Examiner*—Donald O. Woodiel
*Attorney, Agent, or Firm*—Stephen C. Macevicz

[57] ABSTRACT

An apparatus is provided for sensing changes in pressure and for generating optical signals related to said changes in pressure. Light from a fiber optic illuminates a fluorescent composition causing it to fluoresce. The fluorescent composition is caused to more relative to the end of the fiber optic in response to changes in pressure so that the intensity of fluorescent emissions collected by the same fiber optic used for illumination varies monotonically with pressure.

23 Claims, 10 Drawing Figures

PRESSURE-SENSITIVE OPTRODE

The U.S. Government has rights in this invention pursuant to Contract No. W-7405-ENG-48 between the U.S. Department of Energy and the University of California, for the operation of Lawrence Livermore National Laboratory.

CROSS REFERENCE TO RELATED APPLICATIONS

This application is a continuation-in-part of application Ser. No. 430,578 filed Sept. 30, 1982, now U.S. Pat. No. 4,509,370.

BACKGROUND OF THE INVENTION

The invention relates to optical means for remotely measuring pressure and, particularly, for invasive, or direct, measurement of arterial blood pressure.

In medicine, invasive measurement of arterial blood pressure is necessary in the management of critically ill patients or those undergoing complex surgical procedures. Two methods are currently available for direct blood pressure measurements. The first, and most widely used, involves insertion of a fluid-filled catheter into an artery so that the arterial lumen is hydraulically coupled to an external pressure sensing device. Highly accurate arterial pressure-pulse measurements are difficult, if not impossible, however, because the natural frequency of the hydraulic coupling coincides with frequencies of physiological interest. Moreover, the frequency response is variable, depending on the length of the catheter tubing and other unpredictable factors, such as the presence of small bubbles, leaks, or overly compliant plastic tubing used as connectors. These latter factors have impeded attempts to electronically compensate for the undesirable characteristics of the hydraulic coupling.

The other method of direct arterial blood pressure measurement involves the use of miniature solid state or strain-gauge transducers mounted on the tip of a catheter. Although catheter-tip manometers introduce little or no distortion into the pressure signal, a number of practical problems restrict their routine clinical use. The transducers are expensive, and their fragility limits the number of uses for a single catheter. They exhibit DC electrical drift, requiring the use of a fluid-filled lumen or separate catheter to obtain absolute values of arterial pressure. Also, there have been reported instances of mechanical failure of the catheter tip, introducing additional clinical hazards.

In the area of industrial process control, monitoring reactor-vessel pressure is critical for safe and automated operation of nuclear power plants. Pressurized water and boiling water reactors operate at pressures ranging from 1000-1500 psi and temperatures ranging from 250°-350° C. Such conditions, together with the corrosive effects of water and high radiation levels, limit the choice of sensors available for monitoring pressure. Mechanical pressure transducers, such as bellows and diaphragms, are frequently used. However, the transducers are typically external to the reactor vessel, and require that pressure signals be transmitted through fluid conduits. Elimination of such instrument piping is highly desirable where toxic or corrosive fluids are involved, or where even minor leaks lead to severe disruptions in plant operation. In addition, tubing interposed between the point of measurement and the transducers adversely affects the system's frequency response.

Strain-gauge pressure transducers are highly accurate and can be used in hostile environments. However, there are drawbacks to their use. If pressure measurements must be precise, and there are wide and sudden changes in ambient temperature, thermal protection is necessary. High-pressure spikes such as those caused by rapid opening or closing of valves can damage the transducers. Finally, signal transmission from a strain-gauge transducer to point of readout is by electrical wiring. While this eliminates the response time lag encountered whenever a fluid signal-transmission medium is used, electrical wiring is subject to corrosion heat damage, and breakage.

Many of the above-mentioned difficulties with current pressure-sensing technology can be overcome by using remote, in situ mechanical transducers coupled to a detector by optical waveguides, or fiber optics. Fiber optics are durable, corrosion-resistant, heat-resistant, and are available in very small diameters, which makes them amenable for use with miniaturized transducers.

Brogardh, in U.S. Pat. No. 4,270,050, dated May 25, 1981, discloses a remote pressure-sensing device which employs a transducer connected to a detector by a fiber optic. Pressure is sensed by measuring stress-induced changes in the absorption spectrum of a material placed in the path of an illumination beam at the site of the transducer. The transducer includes the stress-sensitive material and a means for converting pressure into a mechanical stress directed to the stress-sensitive material.

A problem with materials that have stress-dependent absorption spectra is that the spectral changes are also temperature dependent. Thus, for reasonable accuracy over appreciable temperature ranges, temperature stabilization is required. Another problem involves the need for converting pressure to stress on the sensitive material. The primary transducer for carrying out this conversion can impair the system's response time, and can increase the difficulty of miniaturization.

Ho, in U.S. Pat. No. 4,158,310, dated June 19, 1979, discloses a fiber optical pressure sensor which requires a cable of fibers and a deformable diaphragm having a reflective surface. The cable is divided at one end into two bundles, one of which is irradiated by a light source, and the other which directs reflected light to a detector. The irradiated fibers are distributed randomly among the fibers of the undivided part of the cable, which in turn is directed to the reflective surface of the deformable diaphragm. The other side of the diaphragm is in contact with the pressurized medium. The curvature of the diaphragm increases in response to increases in pressure, so that less light is reflected onto the fibers leading to the detector. Thus, the intensity of light collected by the detector varies inversely with the ambient pressure.

The use of a fiber cable and diaphragm makes miniaturization difficult, if not impossible. Cables also substantially increase the cost of the sensor, especially in remote sensing applications.

The foregoing illustrates the limitations of the current pressure-sensing technology. An alternative to available pressure sensing methods which overcame some of these limitations would be highly advantageous for remote pressure sensing applications, particularly in situ measurement of arterial blood pressure.

SUMMARY OF THE INVENTION

It is therefore an object of this invention to provide an apparatus for remote pressure sensing in hostile or inaccessible environments.

Another object of this invention is to provide a remote pressure-sensing apparatus which generates an optical signal related to the magnitude of the pressure sensed and which transmits said optical signal to a detector by a fiber optic.

Another object of this invention is to provide a remote pressure-sensing apparatus utilizing fiber optics which is stable over a wide range of temperatures, extending, on the high end, to temperatures encountered in routine and emergency operation of nuclear, geothermal, and conventional power plants.

Yet another object of this invention is to provide a low-cost, low-maintenance remote pressure sensor compatible with a multi-position monitoring system utilizing optical sensors.

Still another object of this invention is to provide a remote pressure-sensing apparatus which is amenable to miniaturization and to inexpensive and rapid fabrication.

Another object of this invention is to provide a remote pressure-sensing apparatus utilizing fiber optics for high fidelity, direct monitoring of human and animal blood pressure.

Another object of this invention is to provide a pressure-sensitive optrode which comprises a hydraulically-based pressure-transducing element.

These and other objects are attained in accordance with the present invention, wherein (1) a fiber optic is provided through which light from at least one associated light source is transmitted from a first end of the fiber optic to a second end of the fiber optic, (2) light emanating from tne second end of the fiber optic illuminates a fluorescent composition causing it to fluoresce, (3) a resilient means associated with the second end of the fiber optic causes the fluorescent composition to move back and forth along the axis of the fiber optic in response to changes in pressure, and (4) the same fiber optic carrying the illumination beam for exciting the fluorescent composition collects and transmits fluorescent emissions to the first end of the fiber optic where said emissions are separated from the illumination beam and analyzed. The magnitude of the fluorescent signal collected by the fiber optic depends on the intensity of the illumination beam, the type of fluorescent composition used, and the distance of the fluorscent composition from the end of the fiber optic. The invention is operated by placing the resilient means in contact with the fluid whose pressure is to be monitored. The resilient means causes the fluorescent composition to move toward the second end of the fiber optic whenever pressure increases and to move away from the second end of the fiber optic whenever pressure decreases. Thus, with constant illumination intensity, high pressures give rise to more intense signals and lower pressures give rise to less intense signals. Preferably, the range of movement of the fluorescent composition substantially includes a region of maximal sensitivity adjacent to the end of the fiber optic. This region is roughly defined by the numerical aperture of the fiber optic and is described more fully below.

The present invention is addressed to problems associated with remote pressure monitoring in hostile or inaccessible regions. It advantageously overcomes many of these problems by combining rugged, high quality fiber optics with simple in situ transducers for generating optical signals related to ambient pressure. For blood pressure measurements, the problem of poor frequency response is overcome by the in situ pressure transducer and by the availability of small-diameter, catheter-sized communications-type fiber optics and hydraulically based resilient means for transducing changes in pressure to displacements of a fluorescent composition. For hostile environments involving high temperatures, high pressures, corrosives, and the like, the problem of providing reliable and durable in situ pressure sensors is overcome by the availability of mechanical transducers fabricated from durable alloys, such as zirconium, stainless steel, nickel alloys, and the like; by the availability of strong, heat-resistant, corrosion-resistant fiber optics; and by the ability to combine these elements to form simple, yet effective pressure sensors, based on the principles taught by the present invention.

In addition, all particular embodiments of the invention are amenable for use with a multi-position sensing system which comprises many sensors, all of which feed signals to a single station for analysis. Such a configuration can reduce costs by obviating the need for separate analyzers for each sensor, and can increase reproducibility between sensors by having all signals analyzed by the same instrument.

BRIEF DESCRIPTION OF THE DRAWINGS

Further objects of the invention, together with additional features contributing thereto and advantages accuring therefrom will be apparent from the following descriptions of preferred embodiments of the invention which are shown in the accompanying drawings, which are incorporated in and form a part of the specification. In the drawings.

DETAILED DESCRIPTION OF THE INVENTION

Figure 1:
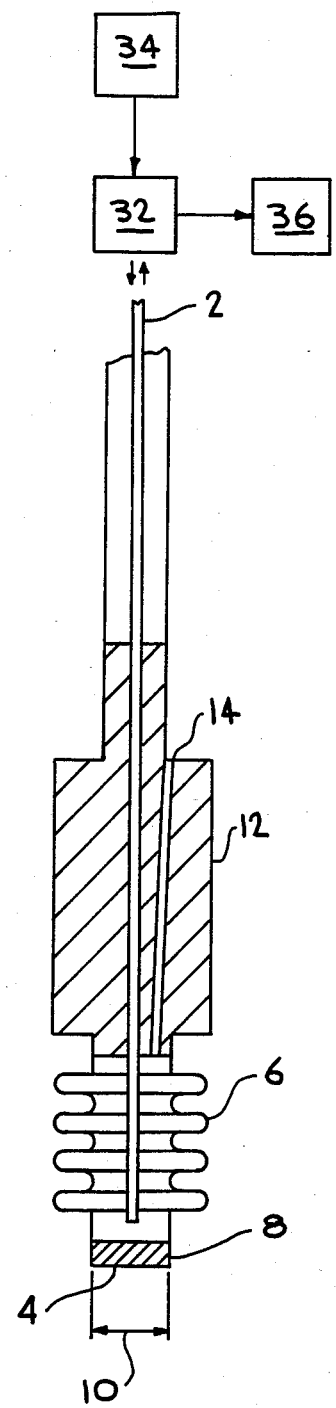
FIG. 1 is a cross-sectional view of a pressure-sensitive optrode incorporating a bellows as the resilient means.

Reference will now be made in detail to the present preferred embodiments of the invention, examples of which are illustrated in the accompanying drawings.

In accordance with the present invention an apparatus is provided for measuring fluid pressure via an in situ fluorescent probe which mechanically or hydraulically couples changes in fluid pressure to changes in fluorescent signal intensity. A resilient means, e.g., a bellows, diaphragm, fluid column in a tube, or the like, attached to one end of a fiber optic constitutes the mechanical or hydraulic coupling. The resilient means causes a fluorescent composition to move back and forth relative to the end of the fiber optic in response to changes in pressure. Light emanating from the fiber optic illuminates the fluorescent composition inducing it to fluoresce. The same fiber optic collects a portion of the fluorescent emissions.

The magnitude of the optical signal collected by the fiber optic depends in part on the numerical aperture of the fiber optic and in part on the distance of the fluorescent emitters from the end of the fiber optic. Light collected by a fiber optic is transmitted essentially loss free along the length of the fiber optic only if it enters the fiber at an angle less than or equal to a characteristic angle (depending on the composition of the fiber optic) from the normal to the end face of the fiber optic. Because of this, the space adjacent to the face of the fiber can be divided into three regions according to whether all, some, or no light emanating from a point in the adjacent space and impinging on the face of the fiber core will be transmitted by the fiber. In a step-index fiber optic the regions are defined by two concentric cones, as shown in cross section by lines 78, 78', 79, and 79' in FIG. 5. The conical region defined by the cone shown in cross section by lines 78 and 78' will be referred to as the region of maximal sensitivity. The conical region defined by the cone shown in cross-section by lines 79 and 79' is sometimes referred to as the acceptance cone of the fiber optic, e.g., Kleecamp and Metcalf, "Designer's Guide to Fiber Optics" (Cahners Publishing Company, Boston, Mass., 1978). As mentioned above, the conical regions are a general characteristic of fiber optics and are not a special feature of the embodiment of the invention shown in FIG. 5. Thus, every fiber optic has a region of maximal sensitivity although it may not have the same geometry as that indicated in FIG. 5, e.g., the fiber optic could be of the graded-index variety. The amount of light collected by the fiber from a light-emitting body moving along the axis of the concentric cones is a well-defined monotonically varying function of the distance between the face of the fiber optic and the body. The precise relationship is determined empirically, although theoretical derivations are possible. Once determined the function can be stored in tabular form in the memory of a microprocessor which is part of a detection means operationally associated with the first end of the fiber optic. Alternatively, the function can be embodied in a nonlinear analog compensator network which provides an electrical output directly proportional to pressure.

Preferably, the range of movement of the fluorescent composition during operation substantially includes the region of maximal sensitivity of the fiber optic. That is, the range of movement preferably includes the subregion adjacent to the apex of the conical region defined in cross-section in FIG. 5 by lines 78 and 78'. In this region a single fiber optic used both for fluorescent excitation and collection is more efficient than a multi-fiber system in which separate fibers are used for excitation and for collection. Efficiency here is used in the sense of intensity of signal collected for a given power of the excitation beam. The extent of this region of superior efficiency depends on the numerical apertures of the fiber optics, the distances between the cores of collection fibers and illumination or excitation fibers in the multi-fiber system.

Preferably, the range of movement of the fluorescent composition does not comprise the region between the end of the fiber optic and the apex of the cone defining the region of maximal sensitivity. Signals generated by a fluorescent composition in the region between the apex of said cone and the end of the fiber optic are highly nonlinear and cannot be translated into pressures as reliably as signals generated by the fluorescent composition when positioned distally to the apex of said cone. The distance between the end of fiber optic and the apex of said cone depends on the numerical aperture of fiber optic: The greater the numerical aperture the smaller the distance between the apex of said cone and the end of the fiber optic.

In accordance with the invention a single fiber optic is employed for both illumination and collection. Thus, the invention includes means 32 for separating the outgoing illumination beam from the incoming fluorescence at the first end of the fiber optic, as shown diagramatically in FIGS. 1, 2 and 3, as well as detection means 36, shown diagramatically in FIGS. 1, 2, and 3. Several means are available for such separation, such as a dichroic which separates on the basis of wavelength, an apertured mirror which separates on the basis of the spacial distribution of the incoming and outgoing beams, or the like. Examples of these beam splitting means are provided in Hirschfeld, U.S. patent application Ser. No. 480,844 filed Mar. 31, 1983 (continuation of application Ser. No. 194,684 filed Oct. 6, 1980, now abandoned), which is incorporated by reference. Preferably, the illumination beam is generated by a light source (34 in FIGS. 1, 2 and 3) operating at a frequency at or near the maximum absorption frequency of the fluorescent composition. Suitable light sources include lasers, mercury arc lamps, light emitting diodes, and the like. Detection means 36 includes photoelectric means for measuring the intensity of the collected fluorescence. Such photoelectric means are well-known in the art. For example, *Optical Industry and Systems Purchasing Directory*, Vol. I and II (Optical Publishing Co., Inc., Pittsfield, Mass., 1982), *Photomultiplier Manual* (RCA Corporation, Harrison, N.J., 1970), and *Handbook of Optics*, Section Four, (McGraw-Hill Book Company, New York, 1978) are guides to suitable photoelectric means. Parker, in *Photoluminescence of Solutions* (Elsevier Publishing Company, New York, 1968) provides an extensive discussion of apparatus for measuring fluorescence.

More than one light source operating at different wavelengths may be preferred when fluorescent compositions are used that comprise more than one kind of fluorescent molecule. Each fluorescent molecule has a preferred range of excitation wavelengths. An illumination beam operating within the preferred range readily produces fluorescent emission; an illumination beam operating outside the preferred range induces little or no fluorescence. Thus, where more than one kind of fluorescent molecule is used, optimal performance may call for a plurality of light sources, each operating within a preferred wavelength range of the respective fluorescent molecules. Detection of a plurality of fluorescent signals may call for a plurality of separation means 32 and attendent detection means 36.

As indicated in the examples below, a wide range of fluorescent compositions can be used in accordance with the present invention depending on the intended application and the resilient means employed.

Fluorescent compositions are attached to the resilient means by mixing with a transparent glue or other binding agent, or by soaking a diffuse reflector, such as paper, silica gel and the like, with a solution containing the fluorescent compositions; then attaching the diffuse reflector to the resilient means. Examples of such commercially available fluorescent compositions include fluorescein, eosin, and the like.

Where operability at high temperature is critical, various solid materials capable of lasing are available for use as fluorescent compositions. By way of example, transition metal or rare earth-doped glasses can be used, including, but not limited to uranyl-doped glass. Wafers or powders of the material can be glued to the resilient means, or the material can be deposited on a surface of the resilient means in molten form. Crystalline laser materials, such as ruby or neodymiumdoped crystals and the like, are also suitable fluorescent compositions.

Figures 2, 3:
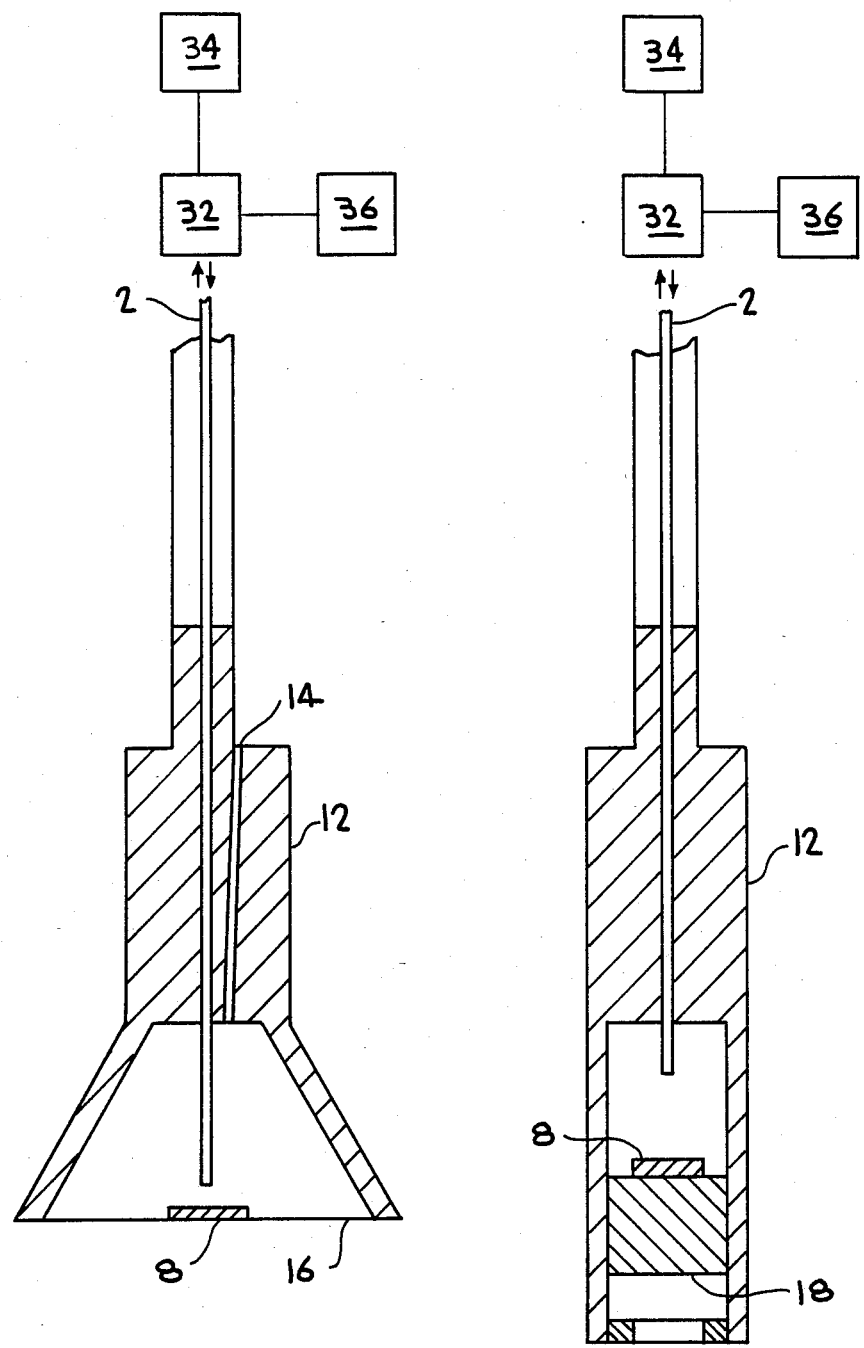
FIG. 2 is a cross-sectional view of a pressure-sensitive optrode incorporating a diaphragm as the resilient means.
FIG. 3 is a cross-sectional view of a pressure-sensitive optrode incorporating a piston as the resilient means.
Figure 5:
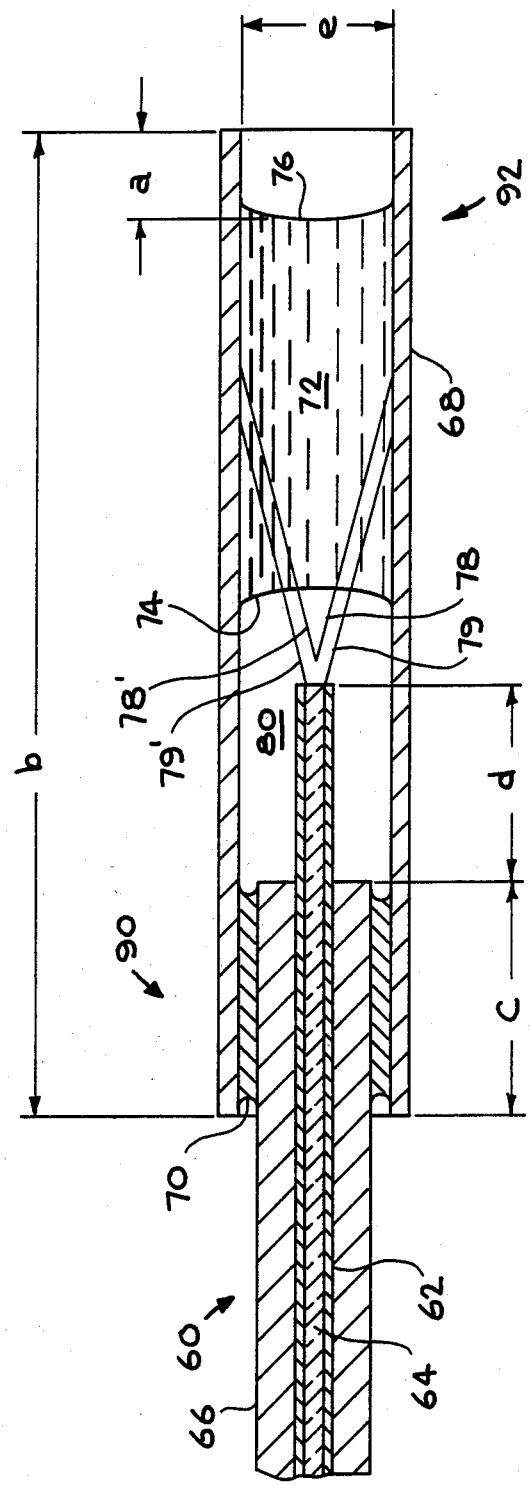
FIG. 5 is a cross-sectional view of a pressure sensitive optrode incorporating a fluid column in a tube as the resilient means.

A large number of pressure-to-motion transducers can be used as resilient means in accordance with the invention, such as bellows 6 in FIG. 1, diaphragm 16 in FIG. 2, piston 18 in FIG. 3, and fluid column 72 and tube 68 in FIG. 5. In the case of the embodiment in FIG. 3, piston 18 moves back and forth within the bore of collar 12, and compresses the gas trapped in the region indicated by 11 whenever ambient pressure increases. Much of the technology associated with the design of pressure-actuated switches is directly applicable to choosing a suitable resilient means for a particular embodiment of the invention. Accordingly, Lyons, *The Designer's Handbook of Pressure-Sensing Device*, (Van Nostrand Reinhold Company, 1980) is incorporated by reference.

The following examples illustrate particular embodiments of the invention, methods of manufacture, and particular applications.

EXAMPLE 1

Bellows as resilient means

FIG. 1 illustrates an embodiment of the invention employing bellows 6 as a resilient means. Fluorescent composition 8 is attached to surface 4 of the bellows. Fiber optic 2 illuminates fluorescent composition 8 and collects the resulting fluorescent emissions. Collar 12 allows bellows 6 to be attached to fiber optic 2 and includes vent 14 so that bellows compression is determined solely by the ambient pressure and the effective spring constant of the bellows. Vent 14 is not critical to the invention.

The choice of a particular bellows is dictated by several factors, such as the operating temperature range, the nature of the pressurized fluid with which the bellows will be in contact, the operating pressure range, the expected frequency of pressure fluctuations, and so on.

For power plant applications, resistance to corrosive fluids, durability, and operability at high, and possibly varying, temperature are crucial design constraints. In the absense of crucial size constraints, commercially available stainless steel bellows can be employed. For use in a nuclear reactor vessel, zirconium bellows can also be fabricated.

Figure 7:
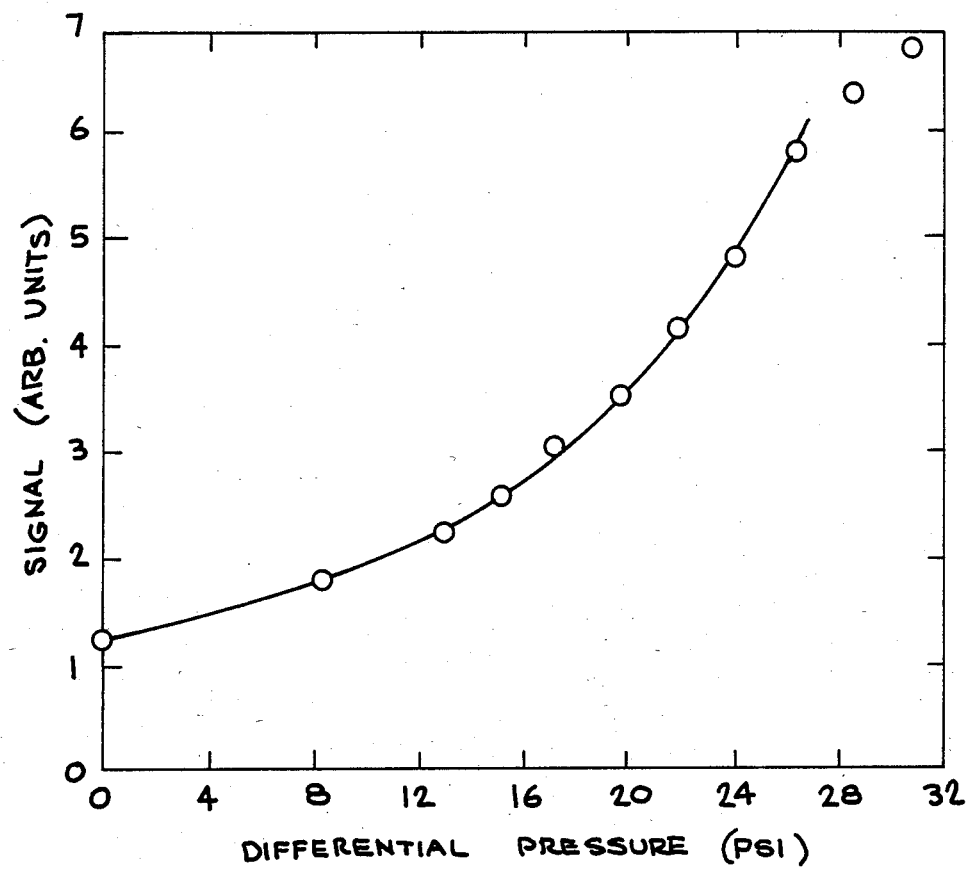
FIG. 7 illustrates relative signal intensity as a function of differential pressure for an embodiment employing a bellows as the resilient means.

A commercially available stainless steel bellows (Servometer Corp., Cedar Grove, N.J.) was employed in one embodiment. The diameter of the bellows, dimension 10 in FIG. 1, was ¼-inch. The stainless steel bellows 6 was silver-soldered onto metal collar 12, which included vent 14. Fluorescent composition 8 comprised filter paper soaked in fluoroscein. Fiber optic 2 was a 200 meter, 200-micron diameter Valtec PC-10 (Valtec Optical Group, Waltham, Mass.). The light source was an argon laser operating at 488 nm and 10 mW, and the photoelectric means was a Spex double monochrometer (Spex Corp., Metuchen, N.J.). FIG. 7 illustrates the relative signal intensity as a function of differential pressure for this embodiment.

EXAMPLE 2

Miniaturized Resilient Means

Another embodiment especially amenable to miniaturization employs a resilient means which comprises plastic bubble 40 with interior 42 (in FIG. 4) attached to the second end 44 of fiber optic 46, that is, the distal end of fiber optic 46 relative to the detection means and the light source.

Figure 4:
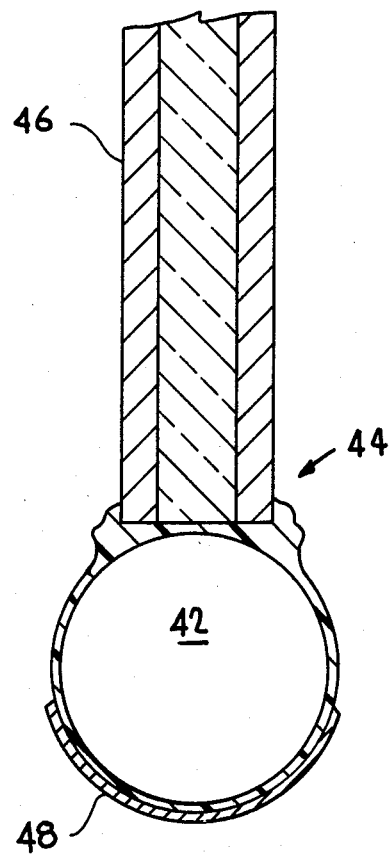
FIG. 4 is a cross-sectional view of a pressure-sensitive optrode incorporating a plastic bubble as the resilient means.

A fluorescent composition can either be mixed with the plastic material forming bubble 40 or the fluorescent composition can be attached as a coating, as illustrated by 48 in FIG. 4. Bubble 40 of this embodiment of the pressure-sensitive optrode can be formed in at least two ways. First, a mixture is formed which comprises a plastic dissolved in a volatile solvent. Second, a small quantity of the mixture is placed on the second end of the fiber optic. And third, an illumination beam is directed into the first end of the fiber optic at an elevated power level, so that the attached droplet of mixture begins to heat and a bubble 40 forms. A second method of constructing this embodiment includes steps of dissolving a plastic in a vessel containing a volatile solvent, agitating the resulting solution until small bubble form at the surface of the liquid, attaching one of the preformed bubbles to the second end of the fiber optic, and allowing the volatile solvent to evaporate, leaving the plastic bubble 44 attached to second end 40 of fiber optic 46. A fluorescent composition may be applied to the outside of the bubble. By way of example, the first of the abovedescribed methods for constructing a miniature optrode has been implemented with collodion (J. T. Baker Chemical Co., Phillipsburg, Pa.), a nitrocellulose based plastic (U.S.P. specifications: pyroxylin 40 g, ether 750 ml, alcohol 250 ml). A droplet, approximately 0.05 milliliters, is placed on the end of a Valtec PC-10 fiber optic (Valtec Optical Group, Waltham, Mass.). A beam of light from an argon laser, operating at 488 nm, at approximately 1 watt, and for approximately 30 seconds, was used to form bubble 40. After cooling, the bubble was coated with a thin layer of fluorescein. The operating power of the illumination beam was approximately 100 milliwatts. Since the bubbles attached to the end of the fiber optic may be chosen so that their diameters are no larger than the diameter of the fiber optic, this embodiment is particularly well adapted to applications where miniature pressure sensors are required.

EXAMPLE 3

Fluid Column in a Tube as Resilient Means

FIG. 5 is a cross section of an embodiment employing a fluid column in a tube as the resilient means. Fiber optic 60, with cladding 62, core 64, and protective sheath 66, is fixedly attached to a first end 90 of tube 68.

Fixing means 70 for attaching fiber optic 60 to tube 68 can be an adhesive, such as an epoxy, cyanoacrylate, or cellulose adhesive, or the like. Alternatively, where the tube comprises a glass capillary tube, the tube may be welded to the end of the fiber optic. For medical applications, tube 68 preferably comprises a catheter-sized tube, i.e., a tube amenable to insertion into the lumen of a vein or artery, made of material resistant to corrosion by physiological fluids, such as glass, plastic, stainless steel, nickel, nickel alloys, or the like. More preferably tube 68 comprises a catheter-sized tube less than a millimeter in diameter. It is important that fixing means 70 form an air-tight seal between the end of fiber optic 60 and tube 68. An air space, or bubble of trapped gas, 80 surrounding the second end of the fiber optic is compressed when increasing pressure drives a column of fluid 72, having a first surface 74 and a second surface 76, toward fiber optic 60.

Preferably the range of movement of column 72 through the bore of tube 68 should substantially include the region defined by the cone (shown in cross section in FIG. 5 by lines 78 and 78') adjacent to its apex, i.e., the region of maximal sensitivity described above.

The fluid column 72 comprises a fluorescent material mixed with any fluid which is sufficiently viscous to remain in the bore of tube 68 and which is immiscible with the fluid whose pressure is to be determined. The fluid containing the fluorescent material is referred to as the carrier fluid. For physiological uses, hydrophobic fluids are preferred as the carrier fluid, such as fats or waxes. Fats are especially preferred because they are non-toxic, they can be mixed to obtain a wide range of melting points, and there are many fat soluble fluorescent materials. Fats with melting points above room temperature and below body temperature are most preferred for invasive blood pressure measurements. Such melting points allow the optrode to be handled and transported with the fat in solid form, which lessens the chances of contamination or loss of the fluid column 72. By way of example, olein, palmitin, and stearin can be mixed in various proportions to obtain melting points between room temperature and body temperature. For a guide to other fats which can be used in accordance with the present invention, see Baily, *Melting and Solidification of Fats* (Interscience Publishers, New York) and Markley, *Fatty Acids,* 2nd edition (Interscience Publishers, New York).

A host of fluorescent molecules can be used in accordance with the present embodiment. Fat soluble fluorescent molecules are preferred and, when structural formulas are available, can be selected according to ordinary solubility rules for organic molecules, e.g., Shugar, et al., *Chemical Technicians' Ready Reference Handbook,* Second Edition (McGraw-Hill Book Co., San Francisco, 1981). Further selection can be made empirically. Many classes of fat soluble fluorescent molecules used as scintillator solutes are applicable for use in the present embodiment, e.g., p-Oligophenylenes, such as p-quaterphenyl; oxazole and oxadiazole derivatives, such as 2,5-diphenyloxazole (the common scintillator solute PPO); and other ring systems such as benzene, naphthalene, pyridine, pyrrole, indole, and the like. Wehry and Rogers, in chapter three of *Fluorescence and Phosphorescence Analysis,* Hercules, editor (Interscience Publishers, N.Y., 1966), discuss generally the fluorescence of organic molecules used in scintillation detectors. Other fat soluble fluorescent molecules suitable for use in the present embodiment include, but are not limited to, methyl eosin, rhodamine 6G, rhodamine 3G, phosphine, tetracycline, chromoxane brilliant red BL, chlorophyll, alizarin rubinol, evans blue, procion yellow, cryptocyanine, pyrene, rubrene, N-phenylnaphthylamine, victoria blue B, 7-ethoxyresorufin, 2-hydroxystilbamidine, parinaric acid, sempervirene, 1,6-diphenylhexatriene, P-quaterphenyl, tetraphenylbutadiene, anthracene, bis-P-methylstyrenylbenzene, stilbene, terphenyl, vitamin A, and vitamin E.

Non-hazardous fat soluble fluorescent molecules are preferred for medical uses. Whether a particular fat soluble fluorescent molecule can be used in a non-hazardous manner depends on several considerations: (1) concentration of the fluorescent molecules necessary to generate measurable signals, (2) blood concentrations and durations of such concentrations that can cause toxic or genotoxic effects, and (3) the rate at which the fluorescent molecules leaks into the blood stream during operation.

More preferably, the fluorescent material comprises fluorescent particles dispersed in the carrier fluid, e.g., powders, microspheres, microencapsulated fluorescent dyes, and the like.

Techniques for microencapsulating fluorescent dyes are described in Mosbach, ed., *Methods in Enzymology,* Vol. 44, "Immobilized Enzymes" (Academic Press, NY, 1976); Vandegaer, ed., *Microencapsulation Processes and Applications,* (Plenum Press, NY, 1975), and Kondo, *Microcapsule Processing and Technology* (Marcel Dekker, Inc., NY, 1976). Fluorescent microspheres are the most preferred fluorescent material. Fluorescent microspheres suitable for use with the present embodiment are available commercially either in forms made from fluorescent compositions or in forms which can be rendered fluorescent by covalently attaching fluoresecent molecules (e.g., Polyscience, Inc. (Warrington, Pa.) and Covalent Technology Corporation (Redwood City, Calif.) provide a variety of microsphere sizes and types suitable for use with the present embodiment). In either form fluorescent microspheres are less likely to diffuse out of the carrier fluid than fluorescent molecules. Consequently, such fluorescent materials are safer, and the choice of applicable fluorescent molecules can be increased by covalently bonding otherwise unacceptably mobile or toxic molecules to microspheres.

For medical or veterinary applications the optrode must either be constructed from materials which do not induce blood coagulation (or more precisely, thrombogenesis) or be treated with agents which prevent blood coagulation. Such materials and treatments are well known in the art. For example, Lemm, et al., *Medical and Biological Engineering and Computation,* Vol. 18, pp. 521–526 (1980); and Francis, U.S. Pat. No. 4,387,183 provide lists of commercially available thromboresistant materials (or materials that can be rendered thromboresistant). Joh, U.S. Pat. No. 4,329,383; Hammar, U.S. Pat. No. 4,326,532; and Joh, U.S. Pat. No. 4,415,490 contain reviews of methods for rendering materials thromboresistant. Maugh, *Science,* Vol. 217, pp. 1129–1130 (1982) discusses the use of albumin coatings for reducing thrombogencicity. The preferred method of treatment is heparinization. The Joh and Hammar patents cited above deal primarily with methods of heparinization. Heparinization can be accomplished in several ways. For example, several commercial heparin coatings are available, such as Glassclad HP (a tradenamed product from Petrarch Systems, Bristol, Pa.) for heparinizing glass surfaces and TDMAC (tri-dode cylmethyl-ammonium chloride) - heparin (available from Polysciences, Inc., Warrington, Pa.). In the event that a fluorescent fluid comprising a fat or fats possesses thrombogenic activity, it can be rendered nonthrombogenic by treatment with TDMAC-heparin. The TDMAC moiety of TDMAC-heparin has a lipophilic hydrocarbon chain which anchors the heparin moiety on second surface 76 of the column of fluorescent fluid 72, thereby rendering it non-thrombogenic.

EXAMPLE 4

Manufacture of Resilient Means Comprising a Fluid Column in a Tube

The first step in the preferred method of manufacturing the optrode employing a fluid column in a tube as resilient means is coaxially positioning and fixedly attaching the second end of the fiber optic 60 to the first end 90 of tube 68 of predetermined inside diameter, indicated by dimension "e" in FIG. 5. Preferably, protective sheath 66 of the second end of fiber optic 60 is removed over a distance from the end face, indicated by dimension "d" in FIG. 4. Removing the protective sheath creates a larger bubble volume 80 which, in turn, allows the column of fluid 72 a greater range of travel for a given variation in pressure. As mentioned above the range of travel of the column of fluid 72 depends on bubble volume 80 and inside diameter of tube 68. The best values for these parameters for a given application are determined empirically. The preferred range of travel for operation depends on the numerical aperture of the fiber optic, as discussed above. In the embodiment illustrated in FIG. 4 the step of inserting and attaching includes inserting the fiber optic such that the distance, indicated by the letter "c", is known.

Figure 6C:
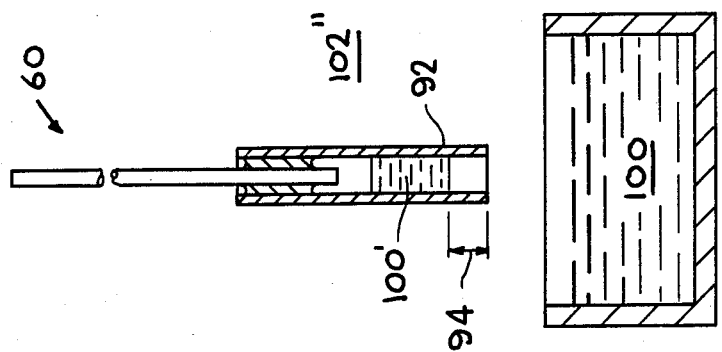
FIGS. 6A–6C illustrate steps of the preferred method of manufacturing the preferred embodiment of the invention which employs a fluid column in a tube as the resilient means.
Figure 6B:
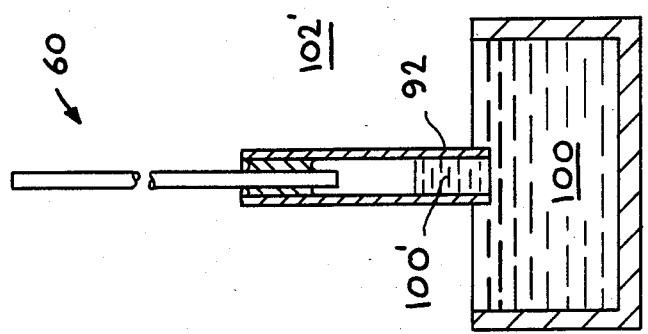
Figure 6A:
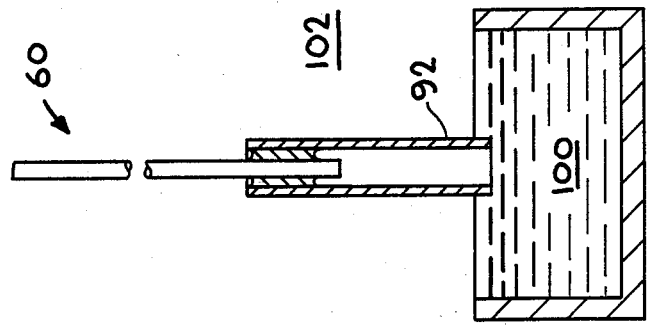

The second step is placing the second end 92 of tube 68 in contact with a reservoir 100 (FIG. 6A) of fluid under conditions wherein the surrounding gas 102 is at a first predetermined pressure, preferably below atmospheric pressure. The third step is increasing the pressure of the surrounding gas 102' in FIG. 6B to a second predetermined pressure (preferably still below atmospheric pressure) while second end 92 of the tube is still in contact with reservoir 100 of fluorescent fluid 100 so that a column 101 of the fluid is forced into the tube. The fourth step is removing the second end of the tube from the reservoir of fluid. The fifth step is increasing the pressure of the surrounding gas 102" (FIG. 6C), preferably to atmospheric pressure, so that fluid column 101 is drawn back from the second end of the tube by a predetermined distance indicated by letter "a" in FIG. 5. Appropriate choices of the first and second predetermined pressures determines how close first surface 74 of the column of fluid 72 is to the end face of fiber optic 60, and how far second face 76 of the column of fluid 72 is recessed from the second end of the tube, i.e., the distance indicated by the letter "a" in FIG. 5. Preferably the temperature is maintained at a level so that the fluid column is in liquid form during the above-described second through fifth steps. The first and second predetermined pressures are determined by straight forward application of the ideal gas law.

For medical and veterinary applications, a step or steps of treating with thromboresistant agents must be made. Before loading the fluid into the tube, the second end of the fiber optic and the tube are treated with a thromboresistant agent. Preferably this step comprises heparinizing. If the fluid contains thrombogenic agents an additional step of heparinizing must be made. For example, when the carrier fluid is a fat, after the fluid is loaded into the tube, the additional step of heparinizing comprises treating second surface 76 of the column of fluid 72 with TDMAC-heparin.

EXAMPLE 5

Figure 8:
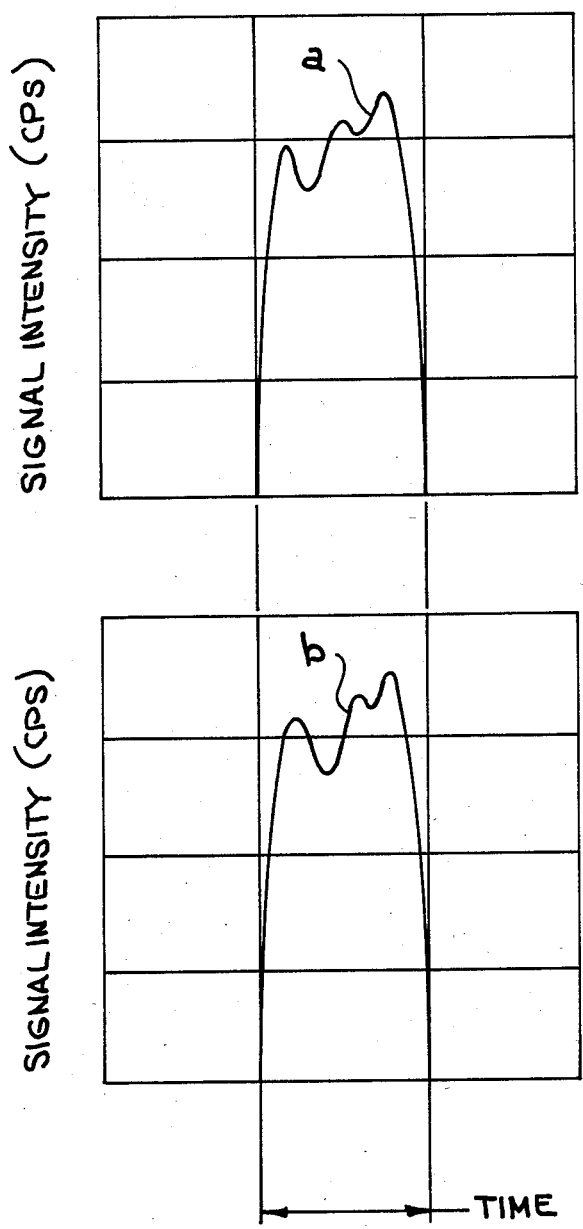
FIG. 8 illustrates the relative signal intensity as a function of time generated by an embodiment of the invention employing a fluid column in a tube as the resilient means.

Operation of an Embodiment Employing a Fluid Column in a Tube as Resilient Means FIG. 8 illustrates the performance of an example of an embodiment of the invention. Curve A of FIG. 8 is a reference pressure signal repeatedly generated by a Model 601A Blood Pressure Systems Calibrator (Bi-oTek Instruments, Inc., Burlington Vt.). Curve B of FIG. 8 is the intensity of the optical signal generated by the particular embodiment in response to the reference pressure. Minor discrepancies between the curves exist because no signal processing means for linearizing the optrode's response signal were included in the detection means of the particular embodiment. The preferred embodiment includes such signal processing means. The particular embodiment comprised a fiber optic (140 $\mu$m cladding diameter, 100 m core diameter, e.g., model S-140 from General Fiber Optics, Caldwell, N.J.) coaxially inserted approximately 300 $\mu$m into a glass capillary tube (300 $\mu$m inside diameter and 0.53 cm in length) and glued in place with an epoxy adhesive. The fluorescent fluid comprised water with 300 ppm fluoroscein. The fluorescent fluid was loaded into the capillary tube so that first surface 74 of the column extended 500 $\mu$m into the tube from second end of the tube.

EXAMPLE 6

Dual Pressure-Temperature Sensor

Ruby affords a means of constructing a dual pressure-and-temperature-sensitive optrode within the purview of the subject invention. Ruby fluoresces at two closely spaced wavelengths, designated the $R_1$ and $R_2$ lines. The relative intensity of the two lines is a function of ambient temperature. Total signal intensity depends on both pressure and temperature. However, by measuring the relative intensity of the $R_1$ and $R_2$ emissions, not only can the temperature be determined, but also the temperature-dependent contribution to the total fluorescent intensity can be factored out to give an accurate pressure reading.

This embodiment requires a special detection means for analyzing the fluorescent signal generated by the optrode. First, the detection means has a stored table of ordered pairs relating the values of the $R_1/R_2$-intensity ratios to ruby temperatures. This table is referred to as the "stored temperature-ratio table." Second, the detection means has the capability of separately measuring the intensity of the $R_1$ emission line, collected and separated from the illumination beam, the intensity of the $R_2$ emission line, collected and separated from the illumination beam, and the intensity of the total fluorescence collected and separated from the illumination beam. This latter intensity is referred to as the "actual total fluorescence." By measuring the intensities of the $R_1$ and $R_2$ emission lines, the $R_1/R_2$-intensity ratio is formed, and the ruby temperature can be read from the stored temperature-ratio table. Third, the detection means has a stored table of ordered pairs relating total ruby fluorescence to ruby temperature under the condition that the ruby is at a predetermined distance from the second end of the fiber optic. This table is referred to as the "stored temperature-intensity table." A value of total ruby fluorescence can be read from the stored temperature-intensity table, once the ruby temperature is obtained from the stored temperature-ratio table. Fourth, the difference between the total ruby fluorescence obtained from the stored temperature-intensity table and the actual total fluorescence is computed. This difference is referred to as the computed difference. Fifth, the detection means has a table of ordered pairs that relates differences between actual total fluorescences and total ruby fluorescences from the stored temperature-intensity table to pressures. This table is referred to as the "stored pressure-intensity difference table." A value for pressure is read from the stored pressure-intensity difference table, once the computed difference is obtained. The special detection means requirements for this embodiment are readily carried out with the assistance of a data acquisition computer, such as a DEC LSI-11 (Digital Equipment Corp., Waltham, Mass.).

Another advantage of ruby is that the range of preferential wavelengths for fluorescent excitation includes the output wavelength of helium-neon lasers. Therefore, these inexpensive and readily available lasers can be used as light sources for pressure optrodes employing ruby as their fluorescent compositions.

EXAMPLE 7

Measurement of Salt Concentration

The subject invention can be adapted to measuring changes in salt concentrations by sensing changes in osmotic pressure across a predetermined semi-permeable membrane. Such an adaptation requires that the resilient means of the pressure-sensitive optrode be enclosed by a hollow body with at least one port. The predetermined semi-permeable membrane covers the port so that only water or selected ions can enter the hollow body. By way of example, the hollow body could be a hollow cylinder surrounding the resilient means attached to the second end of the fiber optic by one end and open at the other end. In this example, the port is the open end of the cylinder.

The concentration of a known salt can be monitored by choosing a semi-permeable membrane impermeable to the known salt, but permeable to the surrounding solvent. A quantity of the known salt is placed inside the hollow body so that the concentration inside the hollow body is the same as the concentration outside the hollow body. Under these conditions, no osmotic pressure is generated inside the hollow body; therefore, no change occurs in the optical signal generated by the optrode. If the exterior salt concentration changes, however, osmotic pressure arises inside the hollow body, causing the resilient means to move closer to or farther away from the second end of the fiber optic, depending on whether the outside concentration change is an increase or decrease. In either case, the optical signal generated by the optrode makes a corresponding change.

The foregoing descriptions of the preferred embodiments of the invention have been presented for purposes of illustration and description. It is not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. An apparatus for monitoring changes in pressure of an associated fluid and for generating optical signals related to said changes in pressure, the apparatus comprising:
   (a) a fiber optic through which an illumination beam from at least one associated light source is transmitted from a first end of the fiber optic to a second end of the fiber optic, the second end of the fiber optic having an end face and a conical region of maximal sensitivity, and the conical region having an apex;
   (b) a fluorescent composition positioned adjacent to the second end of the fiber optic so that the illumination beam emanating from the second end of the fiber optic impinges on the fluorescent composition causing it to generate fluorescent light; and
   (c) resilient means operationally associated with the second end of the fiber optic and the associated fluid whose pressure is to be monitored, the resilient means causing the fluorescent composition to move normally to the end face of the second end of the the fiber optic in response to changes in pressure of the associated fluid so that the fiber optic collects and transmits to its first end an amount of fluorescent light related to the pressure of the associated fluid, and the resilient means causing the fluorescent composition to substantially pass through the conical region of maximal sensitivity adjacent to the apex of the conical region in response to changes in pressure of the associated fluid.

2. The apparatus as recited in claim 1 wherein said resilient means is a bubble of elastic material.

3. The apparatus as recited in claim 2 wherein said elastic material is collodion.

4. The apparatus as recited in claim 1 wherein said resilient means is a bellows.

5. The apparatus as recited in claim 4 wnerein said fluorescent composition is a solid material capable of lasing.

6. The apparatus as recited in claim 5 wherein said solid material is ruby.

7. The apparatus as recited in claim 1 wherein said resilient means is a diaphragm.

8. The apparatus as recited in claim 1 wherein said resilient means is a piston.

9. Tne apparatus as recited in claim 1 wherein said resilient means comprises:
   (a) a tube with a first end, and second end, and a bore, wherein said second end of said fiber optic is coaxially attached to the first end of the tube such that an air-tight seal is formed between said second end of said fiber optic and the first end of tne tube; and
   (b) a column of fluid disposed inside the tube, the column having a first surface and a second surface, and the column occluding the bore of the tube such that (1) a bubble of trapped gas is formed adjacent to said second end of said fiber optic, (2) the first surface of the column is adjacent to but not in contact with said second end of said fiber optic, and (3) the second surface of the column is adjacent to and recessed from the second end of the tube.

10. The apparatus as recited in claim 9 wherein said fluid forming said column of fluid is immiscible with said associated fluid.

11. The apparatus as recited in claim 10 further comprising a plurality of particles suspended in said column of fluid, each of the plurality of particles including said fluorescent composition.

12. The apparatus as recited in claim 11 wherein said particles are in the form of microencapsulated fluorescent molecules.

13. The apparatus as recited in claim 11 wherein said particles are in the form of microspheres.

14. The apparatus as recited in claim 13 wherein said fluid of said column of fluid is a fat or a combination of fats.

15. The apparatus as recited in claim 14 wherein said fat or said combination of fats is selected from the group consisting of olein, palmitin, and stearin.

16. The apparatus as recited in claim 15 wherein said second end of said fiber optic and said tube are heparinized.

17. The apparatus as recited in claim 16 wherein said second surface of said column of fluid is heparinized.

18. The apparatus as recited in claim 10 wherein said fluorescent composition comprises at least one kind of fluorescent molecule dissolved in said column of fluid.

19. The apparatus as recited in claim 18 wherein said fluid of said column of fluid is a fat or a combination of fats.

20. The apparatus as recited in claim 19 wherein said kinds of fluorescent molecules are selected from the group consisting of vitamin A, vitamin E, tetracycline, pyrene, rubrene, N-phenylnaphthylamine, 1,6-phenylhexatriene, anthracene, stilbene, and terphenyl.

21. The apparatus as recited in claim 19 wherein said fat or said combination of fats is selected from the group consisting of olein, palmitin, and stearin.

22. The apparatus as recited in claim 21 wherein said second end of said fiber optic and said tube are heparinized.

23. The apparatus as recited in claim 22 wherein said second surface of said column of fluorescent fluid is heparinized.

* * * * *